US006572529B2

(12) United States Patent
Wilk

(10) Patent No.: US 6,572,529 B2
(45) Date of Patent: *Jun. 3, 2003

(54) INTRAPERICARDIAL ASSIST METHOD

(75) Inventor: Peter J. Wilk, New York, NY (US)

(73) Assignee: Wilk Patent Development Corporation, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/900,126

(22) Filed: Jul. 6, 2001

(65) Prior Publication Data

US 2001/0041821 A1 Nov. 15, 2001

Related U.S. Application Data

(63) Continuation-in-part of application No. 09/678,134, filed on Oct. 4, 2000, and a continuation-in-part of application No. 09/426,744, filed on Oct. 25, 1999, now Pat. No. 6,258,021, said application No. 09/426,744, and a continuation-in-part of application No. 09/121,477, filed on Jul. 23, 1998, now Pat. No. 6,155,968, and a continuation-in-part of application No. 09/105,709, filed on Jun. 26, 1998, now Pat. No. 5,971,911, said application No. 09/105,709, is a continuation-in-part of application No. 08/678,479, filed on Jul. 9, 1996, now Pat. No. 5,800,334, said application No. 08/678,479, is a continuation-in-part of application No. 08/286,817, filed on Aug. 5, 1994, now Pat. No. 5,533,958, which is a continuation-in-part of application No. 08/078,567, filed on Jun. 17, 1993, now Pat. No. 5,385,528.

(51) Int. Cl.⁷ .................................................. A61F 1/00
(52) U.S. Cl. ........................................................ 600/16
(58) Field of Search ............................. 600/16, 17, 18; 128/897, 898

(56) References Cited

U.S. PATENT DOCUMENTS

| 5,766,216 | A | 6/1998 | Gangal et al. |
| 5,800,528 | A | 9/1998 | Lederman et al. |
| 5,865,791 | A | 2/1999 | Whayne et al. |
| 5,928,250 | A | 7/1999 | Koike et al. |
| 5,961,440 | A | 10/1999 | Schweich, Jr. et al. |
| 6,155,968 | A | 12/2000 | Wilk |
| 6,258,021 | B1 * | 7/2001 | Wilk |
| 6,387,042 | B1 * | 5/2002 | Herrero |
| 6,402,680 | B2 * | 6/2002 | Mortier et al. |

* cited by examiner

Primary Examiner—Scott M. Getzow
(74) Attorney, Agent, or Firm—R. Neil Sudol; Coleman Sudol Sapone, P.C.

(57) ABSTRACT

A surgical method for assisting cardiac function utilizes a balloon initially in a collapsed configuration. The balloon is inserted into an intrapericardial space about a patient's heart and is disposed about one portion of the patient's heart. The method further includes inflating the balloon in the intrapericardial space to compress one portion of the patient's heart. A lower end portion of the patient's heart is separately compressed by an additional instrumentality to reduce ventricular volume.

19 Claims, 11 Drawing Sheets

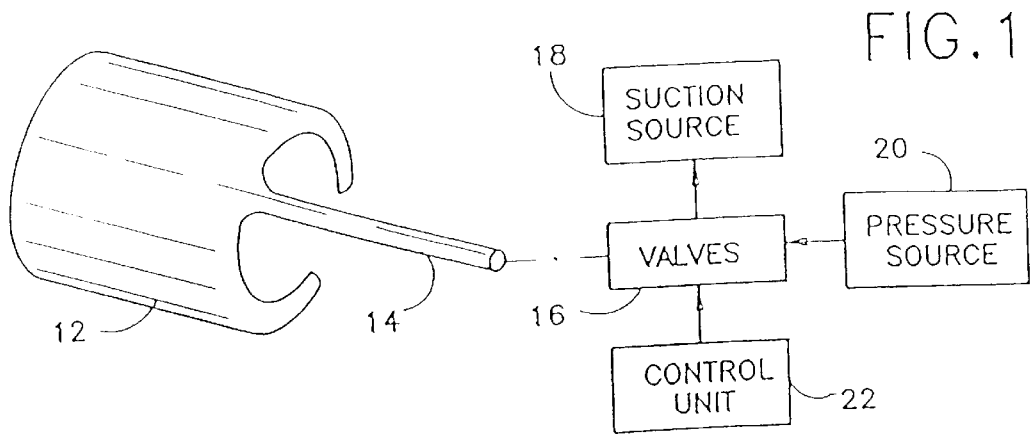
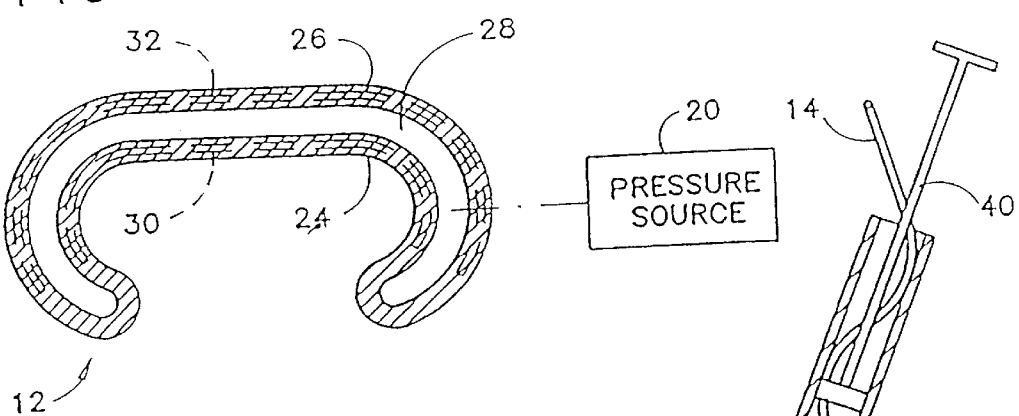
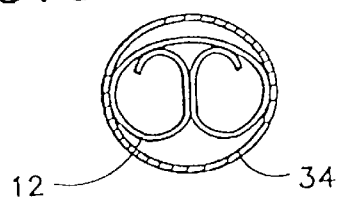
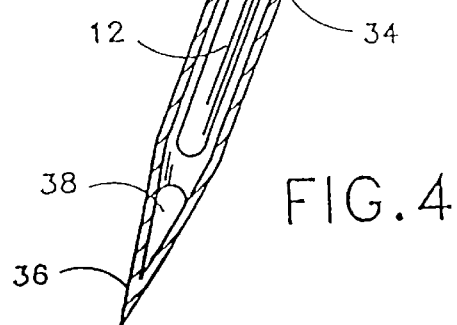

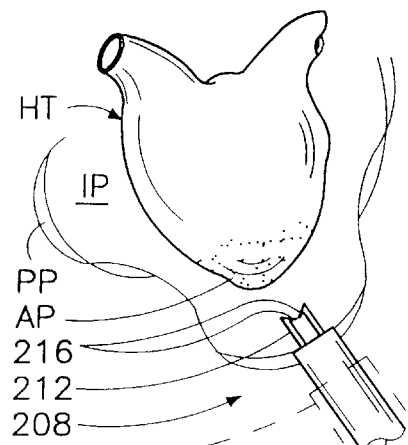
FIG.14A
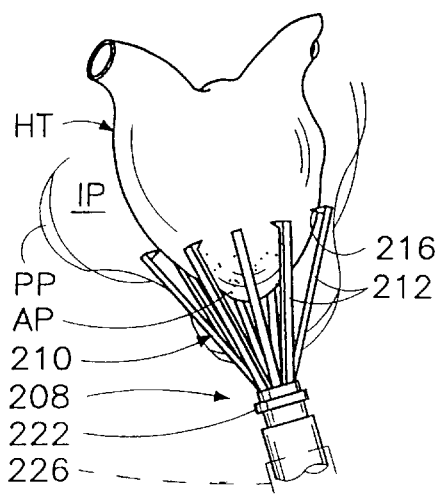
FIG.14B
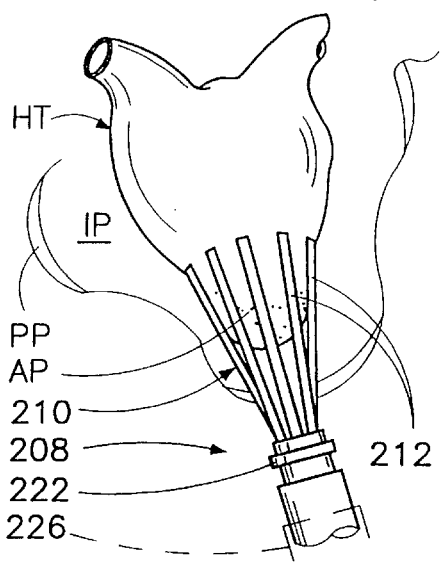
FIG.14C
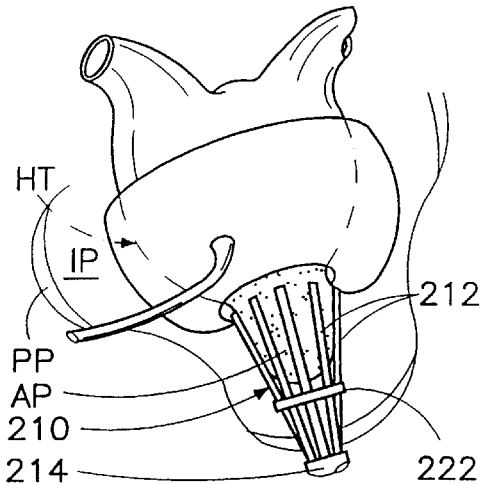
FIG.14D
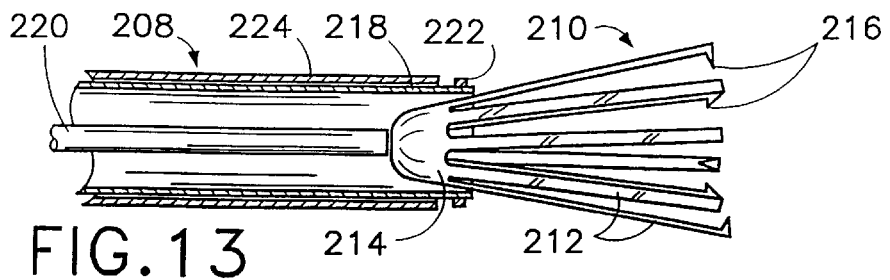
FIG.13
FIG.16A    FIG.16B

INTRAPERICARDIAL ASSIST METHOD

CROSS-REFERENCE TO RELATED APPLICATIONS

This application is a continuation-in-part of application Ser. No. 426,744 filed Oct. 25, 1999, now U.S. Pat. No. 6,258,021, and a continuation-in-part of application Ser. No. 678,134 filed Oct. 4, 2000. Application Ser. No. 426,744 in turn is a continuation-in-part of application Ser. No. 09/121,477 filed Jul. 23, 1998 and of application Ser. No. 09/105,709 filed Jun. 26, 1998, now U.S. Pat. No. 5,971,911. Application Ser. No. 09/105,709 was filed as a continuation-in-part of application Ser. No. 08/678,479 filed Jul. 9, 1996, now U.S. Pat. No. 5,800,334. Application Ser. No. 08/678,479 in turn was filed as a continuation-in-part of application Ser. No. 08/286,817 filed Aug. 5, 1994, now U.S. Pat. No. 5,533,958, which was filed as a continuation-in-part of application Ser. No. 08/078,567 filed Jun. 17, 1993, now U.S. Pat. No. 5,385,528.

FIELD OF THE INVENTION

This invention relates to a method for improving cardiac function. More particularly, this invention relates to an intrapericardial assist procedure. The invention is useful in assisting a patient's heart in its pumping function, even where there is congestive heart failure. This invention also relates to a method for assisting a patient's heart in its pumping function.

BACKGROUND OF THE INVENTION

When a patient's heart stops, for example, in the operating room, cardiopulmonary resuscitation (CPR) is required. In that procedure the chest is violently pounded at the region of the sternum to compress the chest and thereby compress the heart between the sternum and the spine. This compression forces blood out of the ventricles through the one-way valves of the heart. When the pressure on the heart is released, the heart expands and blood is sucked into the heart.

For all its violence, CPR is a delicate procedure in that it must be performed correctly in order to have the desired result of starting the stopped heart. A problem with CPR is that, whether or not it is performed correctly, CPR invariably results in cracked ribs, a fractured sternum and destroyed costo-chondral (cartilage) junctions. Thus even if a patient survives CPR, he is usually injured.

Another serious cardiac condition arises in people who have experienced heart attacks. In such persons, a portion of the heart muscle is frequently destroyed by the attack. Although nerves passing through the damaged heart tissue are not destroyed to the point of ceasing function, the operation of the nerves may be significantly impaired. Conduction of nerve impulses may be delayed. This delay in signal transmission over the impaired nerves results in a delay in heart muscle contraction in those parts of the heart controlled by the impaired nerves. This condition is observed as a "bundle branch block" in an electrocariogram.

Reviving a patent after cardiac arrest is made more difficult when the patient suffers from congestive heart failure. Congestive heart failure occurs, inter alia, where there has been a heart attack or an infection. In either case, the pumping action of the heart is impaired. In another malfunction, left ventricular hypertrophy, the myocardium of the left ventricle becomes thickened to the point of interfering with effective heart contraction. Hypertrophy of the left ventricular muscle arises from a sticky heart valve or aortic stenosis. The increase in left ventricular pressure resulting from increased resistance to blood flow out of the left ventricle gradually induces an increase in the size of the myocardium about the left ventricle. This left ventricular hypertrophy is a dangerous condition, particularly where the individual suffers from coronary artery disease. The larger heart muscle requires greater blood flow and is therefore more sensitive to even temporary reductions in that flow. Such a reduction in blood flow occurs, for example, when the afflicted individual exercises.

A surgical procedure for treating congestive heart failure, developed by a doctor in Brazil, involves removing a triangular portion of a patient's heart. In this operation, approximately one-third of the patient's left ventricular muscle is removed. The result is that the smaller heart pumps more efficiently. This technique of course requires open heart surgery, with its attendant expense and extended convalescence.

OBJECTS OF THE INVENTION

An object of the present invention is to provide a method and/or an associated device for assisting cardiac function.

A more particular object of the present invention is to provide such a method and/or device which is less traumatic than conventional cardiac treatment techniques.

Another particular object of the present invention is to provide such a method and/or device wherein the device is implanted into the heart or the intrapericardial space.

A further object of the present invention is to provide such a method and/or device which can compensate for or take into account congestive heart failure.

It is another object of the present invention to provide a such method taking into account congestive heart failure which may be carried out through the use of minimally invasive procedures.

An additional object of the present invention is to provide a device for implementing such a surgical method.

Another object of the present invention is to provide such a method and/or device which is of simple construction.

A further, more particular, object of the present invention is to provide such a method and/or device which is implemented at least partially automatically.

These and other objects of the present invention will be apparent from the drawings and detailed descriptions herein. It is to be noted that although every embodiment of the invention is believed to meet one or more of the stated objectives, not every object is necessarily attained in every embodiment of the invention.

SUMMARY OF THE INVENTION

The present invention is directed to a surgical method for assisting cardiac function. Generally, the method comprises an at least partial closure of a lower portion of at least one ventricle of a patient's heart. Optionally, the method also includes applying compressive force to the patient's heart via a balloon inserted into an intrapericardial space about the heart.

Pursuant to one embodiment of the present invention, the method includes inserting a device into a patient and applying the device to a lower end portion of the patient's heart so as to compress and at least partially close a lower portion of at least one ventricle of the heart. The device includes a wire provided at a free end with at least one anchoring barb.

The applying of the device to the lower portion of the patient's heart includes inserting a catheter into a ventricle of the patient's heart and ejecting the free end of the wire from the catheter into the patient's myocardium so that the free end and the at least one barb are embedded in the myocardium, surrounded thereby. Tension is exerted on the wire to pull walls of the patient's heart towards one another so as to compress and close off the lower portion of the at least one ventricle of the heart.

In a more particular execution of the method of the present invention, the free end of the wires is one of a pair of free wire ends each provided with at least one barb, while the applying of the device to the lower portion of the patient's heart includes ejecting the free wire ends from the catheter into the patient's myocardium so that the free ends and the respective barbs thereof are embedded in the myocardium, surrounded thereby. Tension is exerted on the wire ends to pull the walls of the patient's heart towards one another so as to compress and close off the lower portion of the at least one ventricle of the heart.

Pursuant to another feature of the present invention, the wire ends are terminal portions of wire segments and the exerting of tension on the wire ends includes twisting the wire segments about one another.

Where the walls targeted by the wire ends are outer walls of the patient's heart, the applying of the device serves to compress and at least partially close lower portions of two ventricles. Where one of the walls is an outer wall of the patient's heart while another of the walls is a septum of the patient's heart, the applying of the device serves to compress and at least partially close a lower portion of exactly one ventricle. In this latter case, the ejecting the free end of the wire from the catheter into the patient's myocardium may include forcing the free end of the wire through the septum of the patient and into the outer wall of the patient's heart.

The method may further comprise inserting at least one balloon into an intrapericardial space about the patient's heart and inflating the balloon in the intrapericardial space to place a compressive pressure on the patient's heart sufficient to force blood from the heart. Generally, the wire device is applied to the lower portion of the patient's heart prior to the inflating of the balloon. In addition, the method possibly comprises periodically inflating and alternately deflating the balloon to pump blood from the heart in pulsatile fashion. The wire device is maintained in the patient's heart to keep the lower portion of the one or two ventricles of the patient's heart compressed and closed off during the periodic inflating and deflating of the balloon.

In accordance with a further feature of the present invention, the inserting of the balloon into the intrapericardial space includes providing a hypodermic type needle, inserting the needle through a skin surface and into the intrapericardial space, and injecting the balloon in a collapsed configuration into the intrapericardial space.

Where the balloon has an arcuate cuff configuration in an inflated configuration, the inflating of the balloon includes shaping the balloon into the arcuate configuration.

Thus, the wire device of the present invention may be deployed in a minimally invasive, intravascular procedure. Alternatively, the wire device may be inserted through a trocar sleeve or cannula.

A method for reducing ventricular volume comprises, in accordance with another embodiment of the present invention, inserting a catheter into a ventricle of a patient's heart, deploying a tensile member from a leading end of the catheter, attaching the tensile member to the patient's heart so that the tensile member is contained completely within the patient's heart and does not protrude therefrom, and exerting tension on the tensile member to draw walls of the patient's heart towards one another to reduce the volume of at least one ventricle of the patient's heart. The tensile member may be provided with at least one barb at a leading end, the attaching of the tensile member to the patient's heart including embedding the barb in the patient's heart. Where the tensile member is one of two tensile members, the method further comprises attaching the other tensile member to the patient's heart, the exerting of tension on the one of the tensile members including twisting the tensile members about one another. As discussed above, the walls drawn together by the tensile may be outer walls of the patient's heart, so that the attaching of the tensile member to the patient's heart and the exerting tension on the tensile member serve to compress and at least partially close lower portions of two ventricles. Alternatively, the walls drawn together by the tensile may be an outer wall of the patient's heart and a septum of the patient's heart, so that the attaching of the tensile member to the patient's heart and the exerting tension on the tensile member serve to compress and at least partially close a lower portion of exactly one ventricle.

In some embodiments of the present invention, the compressive or tensile member may take the form of an elongate tack ejected from a tubular member such a catheter or trocar sleeve or cannula.

It is apparent, therefore, that the present invention is directed in part to a method for reducing ventricular volume, wherein a catheter is inserted into a ventricle of a patient's heart, a cardiac insert or implant is deployed from a leading end portion of the catheter, and the cardiac insert or implant is disposed in the patient's heart to reduce the volume of one or two ventricles of the patient's heart. The cardiac insert or implant is preferably applied to the lower or apical end of the heart. It is contemplated that the cardiac insert or implant takes the form of a tensile member such as a wire or tack which is attached to the patient's heart. However, other forms of inserts or implants may be effective to reduce ventricular volume.

A surgical method in accordance with the present invention treats congestive heart failure. The method may be performed thoracoscopically which is less expensive and less traumatic to the patient than an open-heart surgical technique. The minimally invasive, intravascularly implemented procedure is even less expensive and less traumatic to the patient. The method of the invention is simple and reliable.

A surgical method in accordance with the present invention provides assistance for cardiac function and may utilize a balloon which is initially in a collapsed configuration. The balloon together with an implantable tensile device is inserted into a patient inside the pericardium. More particularly, the balloon is positioned in the intrapericardial space. The secondary device is employed to close off the lower end portion of one or both of the patient's ventricles, the balloon being used to contract or compress the remaining portion of the patient's heart to squeeze blood from the reduced-size ventricle(s).

A method in accordance with the present invention is capable of compensating for differential action of an individual's heart. The method and device are effective when a chamber of the individual's heart experiences excessive pressure levels owing, for example, to a sticky valve or aortic stenosis.

BRIEF DESCRIPTION OF THE DRAWING

FIG. 1 is a partially a schematic perspective view, on a reduced scale, and partially a block diagram of an intrapericardial assist or resuscitation assembly, showing an inflatable intrapericardial cuff in an expanded configuration.

FIG. 2 is a schematic cross-sectional view of the inflatable intrapericardial cuff of FIG. 1.

FIG. 3 is a schematic transverse cross-sectional view of the inflatable intrapericardial cuff of FIGS. 1 and 2 in a folded, collapsed pre-insertion configuration inside a hypodermic type needle.

FIG. 4 is a schematic longitudinal cross-sectional view of the inflatable intrapericardial cuff of FIGS. 1–3 in the folded, collapsed pre-insertion configuration inside the hypodermic needle of FIG. 3.

FIG. 13 is a schematic partial longitudinal cross-sectional view of an instrument or device for operating on the heart to improve cardiac function in conjunction with a pulsatile cardiac pressurization balloon as described, for example, with reference to FIGS. 1–10.

FIGS. 14A–14D are schematic views of a person's heart, showing successive steps in a surgical procedure for improving cardiac function.

DESCRIPTION OF THE PREFERRED EMBODIMENTS

Figure 5:
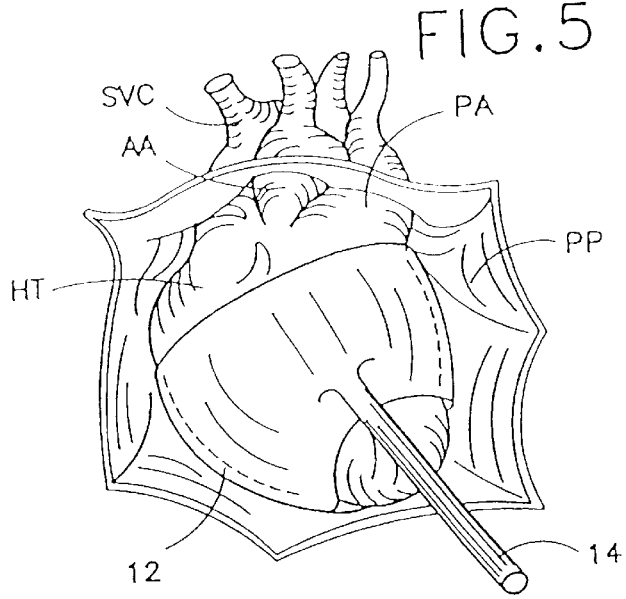
FIG. 5 is a perspective view of the cuff of FIGS. 1–4 in an expanded configuration in place inside an intrapericardial space.

As illustrated in FIG. 1, an intrapericardial assist or resuscitation assembly comprises an alternately inflatable and collapsible balloon 12 in the form of a cuff. Cuff 12 has an elongate tube 14 extending to a valve device 16 which is connected to a suction source or vacuum generator 18 and to a source 20 of pressurized fluid such as water, saline solution or a gas such as air. In response to signals from a control unit 22, valve device 16 periodically connects cuff 12 to pressure source 20 and alternately to suction source 18, whereby cuff 12 is rapidly and forcefully inflated with a predetermined periodicity.

Control unit 22 may be provided with setting knobs (not illustrated) for varying the rate and maximum pressure that is applied to the cuff upon proper disposition thereof in the intrapericardial space about the heart.

As illustrated in FIGS. 1 and 2, cuff 12 has an arcuate, generally C-shaped configuration in its expanded or inflated state. Cuff 12 has a pair of major C-shaped walls 24 and 26 defining a pressurization chamber 28. Embedded in walls 24 and 26 are spring elements or ribs 30 and 32 which can be bent into a curled configuration (see FIG. 3) but which tend to resume their C-shaped expanded configurations when cuff 12 is placed into an intrapericardial space during a cardiopulmonary resuscitation procedure.

As illustrated in FIGS. 3 and 4, prior to a cardiopulmonary resuscitation procedure, cuff 12 is folded and inserted in a collapsed configuration inside a hollow hypodermic type needle 34. Needle 34 is provided at a distal end 36 with an aperture 38 for the ejection of folded and collapsed cuff 12 by a distally directed stroke of a plunger member 40 upon a disposition of distal end 36 into an intrapericardial space during a cardiopulmonary resuscitation procedure. Distal end 36 is also provided with an electrical sensor for detecting the surface of the heart, as is conventional in known intrapericardial sampling needles.

Distal end 36 of intrapericardial needle 34 is inserted into the intrapericardial space through the skin under the patient sternum.

FIG. 5 shows the placement of cuff 12 in an intrapericardial space between a heart HT and the associated surrounding parietal pericardium PP. The diagram also shows the superior vena cava SVC, the pulmonary artery PA, the ascending aorta AA, and other veins and arteries.

Figure 6:
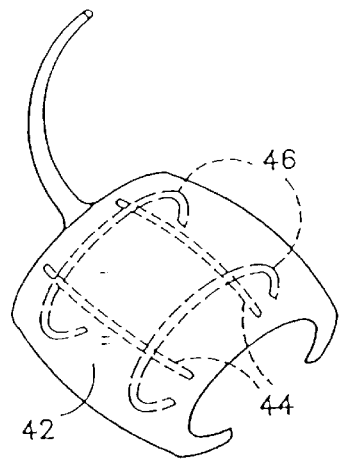
FIG. 6 is another schematic perspective view of an inflatable intrapericardial cuff, showing memory ribs inside the cuff for aiding in an unfolding thereof upon insertion of the cuff into an intrapericardial space.

As depicted in FIG. 6, an inflatable intrapericardial cuff 42 may be provided with a plurality of longitudinally extending ribs 44 and a plurality of transversely extending expansion ribs 46. Each rib 46 has a memory whereby the rib may be bent for insertion and retrieval from a patient's intrapericardial space, but tends to assume a pre-established configuration (FIG. 6) upon insertion of the cuff 42 into an intrapericardial space or cavity.

Figure 7A:
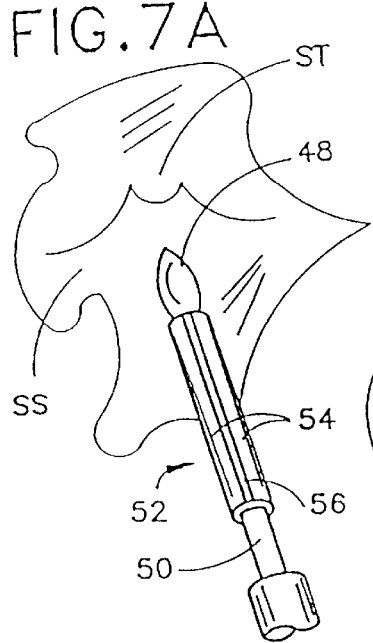
FIGS. 7A–7C are schematic perspective views showing successive steps in one intrapericardial cuff insertion procedure.
Figure 7B:
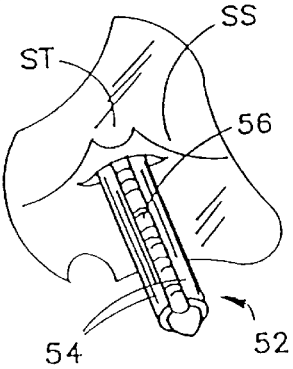
Figure 7C:
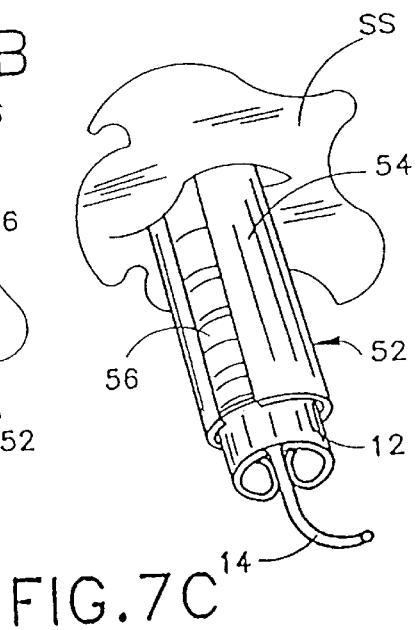

In another cuff insertion procedure depicted in FIGS. 7A–7C, a sharp distal tip 48 of an intrapericardial needle 50 is inserted through a patient's skin SS under the sternum ST. A dilating device 52 comprising a plurality of longitudinal ribs 54 interconnected by stretchable membranes 56 surrounds needle 50 during the insertion procedure. Upon the insertion of distal tip 48 into the intrapericardial cavity at the patient's heart, dilating device is slid in the distal direction so that a distal end portion thereof is disposed or inserted into the intrapericardial cavity. Needle 50 is then removed, as shown in FIG. 7B.

Upon the removal of needle 50 from the patient, leaving dilating device 52 partially inserted into the patient's intrapericardial cavity, the dilating device may be expanded, for example, by the insertion of a series of increasing large elongate rigid dilators (not shown). Then, cuff 12 or 42 is inserted in a folded collapsed configuration into the intrapericardial cavity through the expanded dilating device 52, as shown in FIG. 7C. An inserter (not illustrated) may be used for pushing the cuff through dilating device 52.

The general use and structure of dilating device 52 is described in detail in allowed U.S. patent application Ser. No. 851,097 filed Mar. 13, 1992 and U.S. patent application Ser. No. 893,991 filed Jun. 5, 1992. The disclosures of those applications are hereby incorporated by reference.

Figure 8:
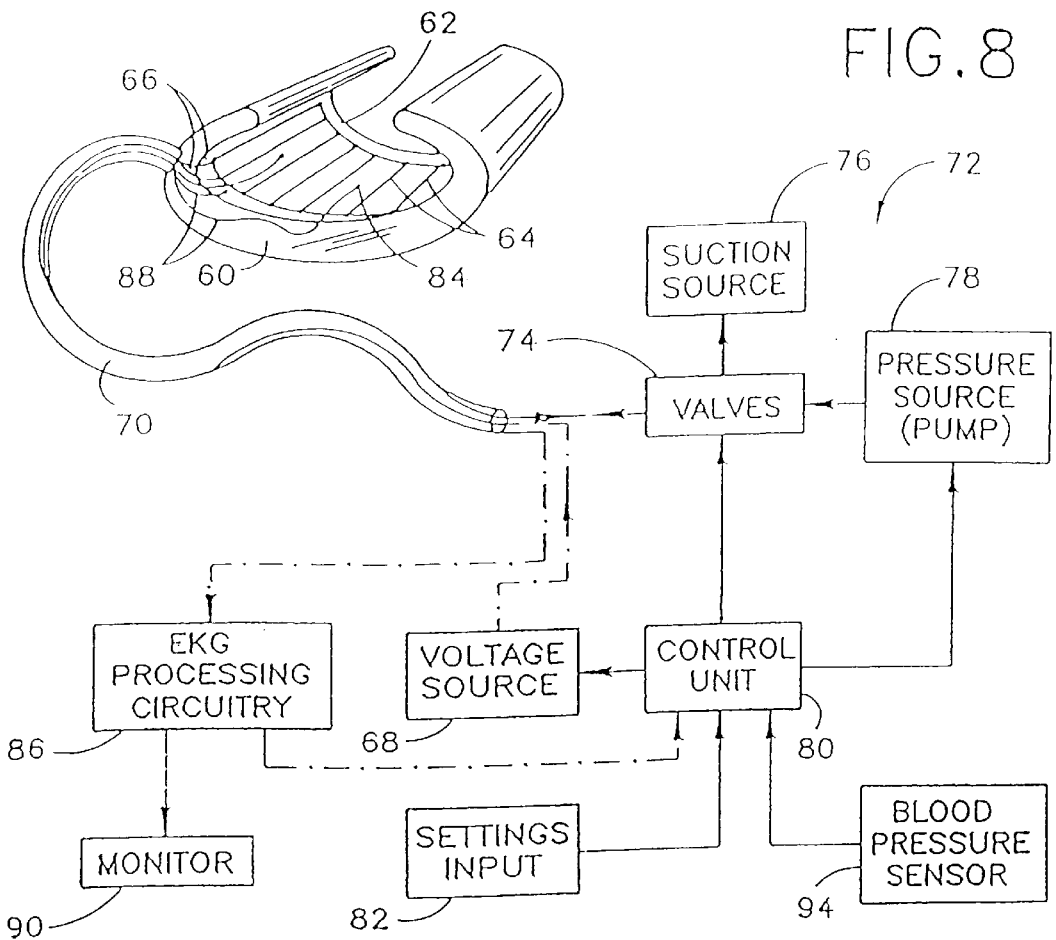
FIG. 8 is partially a schematic perspective view, on a reduced scale, and partially a block diagram of a modified intrapericardial assist or resuscitation assembly, showing an expanded intrapericardial cuff with a voltage source operatively connected to an electrode array along an inner surface of the cuff.

As depicted in FIG. 8, an intrapericardial assist device comprises an electrode carrier in the form of an inflatable balloon 60 adapted for juxtaposition to a patient's heart in an intrapericardial space, as discussed hereinabove with reference to FIG. 5. The electrode-carrying balloon 60 has an inwardly facing surface 62 adapted for contact with the patient's heart. An array of electrical contacts or electrode wires 64 is disposed on contact surface 62 of balloon 60 for conducting electrical energy to the patient's heart upon an insertion of balloon 60 into the intrapericardial space. Current transmission elements or leads 66 are operatively connected to electrical contacts 64 for delivering electrical energy thereto from a voltage source 68. A hose 70 extends to balloon 60 for maintaining the balloon in an inflated state and thereby maintaining the balloon's contact surface 62 in adequate engagement with the patient's heart during the application of electrical energy to the heart via voltage source 68, transmission leads 66 and electrical contacts or electrodes 64.

Balloon 60 is a collapsible member with a configuration of a slotted cuff in an expanded configuration. Balloon 60 has a predetermined size and shape in the expanded configuration so that it is disposable in the intrapericardial space in juxtaposition to the patient's heart. Preferably, one or more spring elements in the form of elongate ribs, e.g. 30, 32 (FIG. 2) or 44, 46 (FIG. 6), are connected to balloon 60 for automatically unfurling the balloon from a folded collapsed insertion configuration to an expanded use configuration.

The means for maintaining contact surface 62 of balloon 60 in engagement with the patient's heart during a cardiac jump start as described herein includes inflation componentry 72 operatively connected to balloon 60 via hose 70. Inflation componentry 72 includes a valve device 74 which is connected to a suction source or vacuum generator 76 and to a source 78 of pressurized fluid such as water, saline solution or a gas such as air or carbon dioxide. In response to signals from a control unit 80 such as a specially programmed microprocessor, pressure source 78 and valve device 74 pressurize balloon 60 to a predetermined pressure during an electrical cardiac stimulation procedure, whereby contacts or electrodes 64 are maintained in electrically conductive contact with a patient's heart. Alternatively, during mechanical heart stimulation as described herein, control unit 80 activates valve device 74 to periodically connect balloon 60 to pressure source 78 and alternately to suction source 76, whereby balloon 60 is rapidly and forcefully inflated with a predetermined periodicity.

Control unit 80 is provided with setting knobs 82 for enabling a preselection of an inflation pressure of balloon 60 and for varying the rate and maximum pressure that is applied to balloon 60 upon proper disposition thereof in the intrapericardial space about the heart.

As further depicted in FIG. 8, a plurality of sensor electrodes 84 is disposed on contact surface 62 of balloon 60 for monitoring natural voltages of a cardiac cycle. Sensor electrodes 84 are connected to EKG processing circuitry 86 via leads 88. According to conventional signal processing techniques, circuitry 86 generates a signal indicative of the patient's heart activity and displays the signal via a cathode ray tube (CRT) or video screen 90. Sensor electrodes 84 and EKG processing circuitry facilitate the monitoring of heart activity during a heart resuscitation or beat regularization procedure as described below.

In a surgical method for reactivating a malfunctioning heart, e.g., a stopped heart or a dangerously arrhythmic heart, balloon 60 is inserted into an intrapericardial space about the patient's heart, as discussed above with reference to FIGS. 5 and 7A–7C. Upon deployment of balloon 60 in the intrapericardial space, the balloon is inflated to place electrodes 64 in electrically conductive contact with the heart. Then, a defibrillating type voltage produced by a generator 92 of voltage source 68 is conducted via leads 66 and electrodes 64 to the patient's heart.

Upon the conduction of the defibrillating type voltage to the patient's heart, heart action is monitored via electrodes 84, processing circuitry 86 and CRT 90 for a predetermined period. If it is determined at that juncture that the patient's heart has started but with an insufficiently strong action, input provided to control unit 80 via setting knobs 82 induces that unit to control valve device 74 so as to inflate balloon 60 forcefully in synchronism with a heart contraction. Synchronism may be achieved, for instance, by providing control unit 80 with input from a blood pressure and pulse sensor 94 (including, e.g., a separate pressure cuff). Alternatively, if balloon 60 is sufficiently inflated, control unit 80 may receive input from EKG processing circuitry 86. In either case, control unit or microprocessor 80 determines when a heart contraction is about to occur and opens valve device 74 to induce a flow of pressurizing fluid along hose 70 to balloon 60. The placement of a compressive pressure on the heart to thereby increase pumping action may alternatively be initiated manually by providing a triggering signal to control unit 80 via setting knobs or input 82.

Balloon 60 may be at least partially deflated upon conduction of the defibrillating type voltage to the heart and prior to the monitoring of the heart action. The deflation may be only partial in the event that the heart action is monitored via sensor electrodes 84 and EKG processing circuitry 86. The deflation may be greater where the cardiac activity is determined via a conventional EKG device separate from balloon 60 and electrodes 84.

To further instill a regular heart beat, a pacemaker type periodic voltage is produced by a generator 96 included, together with generator 92, in voltage source 68. The pacemaker type voltage is applied to the patient's heart via contacts or electrodes 64 upon an inflation of balloon 60 sufficient to ensure electrically conductive engagement between the heart tissues and the electrodes. Control unit 80 regulates the pressurization of balloon 60 via valve device 74 and pressure source 78.

Figure 9:
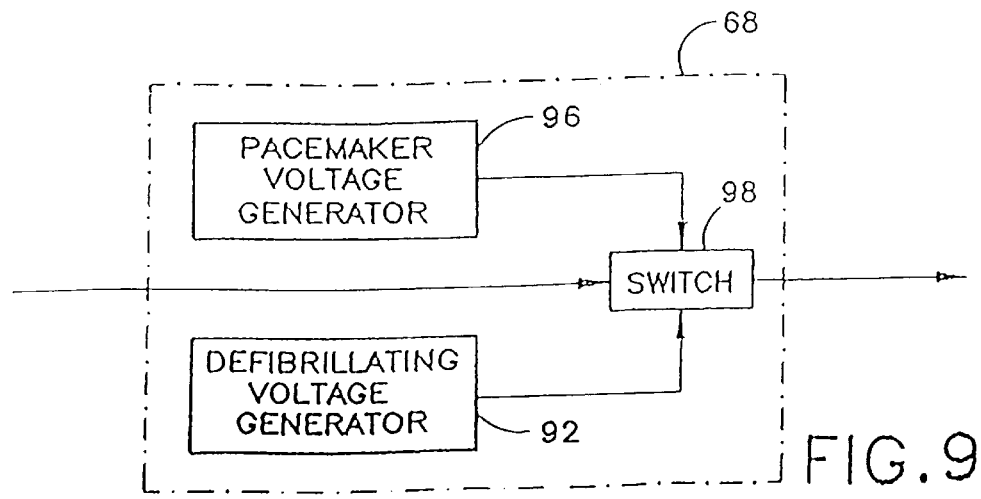
FIG. 9 is a block diagram showing details of the voltage source illustrated in FIG. 8.

The pacemaker type voltage may be applied after a defibrillating procedure as described hereinabove and after periodic cuff inflation to strengthen the heart beat. Control unit 80 determines by the activation of a switch 98 (FIG. 9) whether a defibrillating type voltage or a pacemaker voltage is applied to the cardiac tissues.

As described hereinabove with reference to FIGS. 7A–7C, the insertion of balloon 60 into the intrapericardial space may be implemented using hypodermic type needle 34. Needle 34 is inserted through a skin surface and into the intrapericardial space, balloon 60 being injected in the collapsed configuration through the needle into the intrapericardial space. As further discussed hereinabove with reference to FIGS. 7A–7C, dilating device 52 may be provided for facilitating the insertion of balloon 60 into the intrapericardial space. Needle 50 is partially inserted through the skin surface and into the intrapericardial space and a distal end portion of dilating device 52 is placed into the intrapericardial space via the needle upon the partial insertion thereof into the intrapericardial space. Dilating device 52 is subsequently expanded and balloon 60 inserted into the intrapericardial space through the expanded dilating device.

Figure 10:
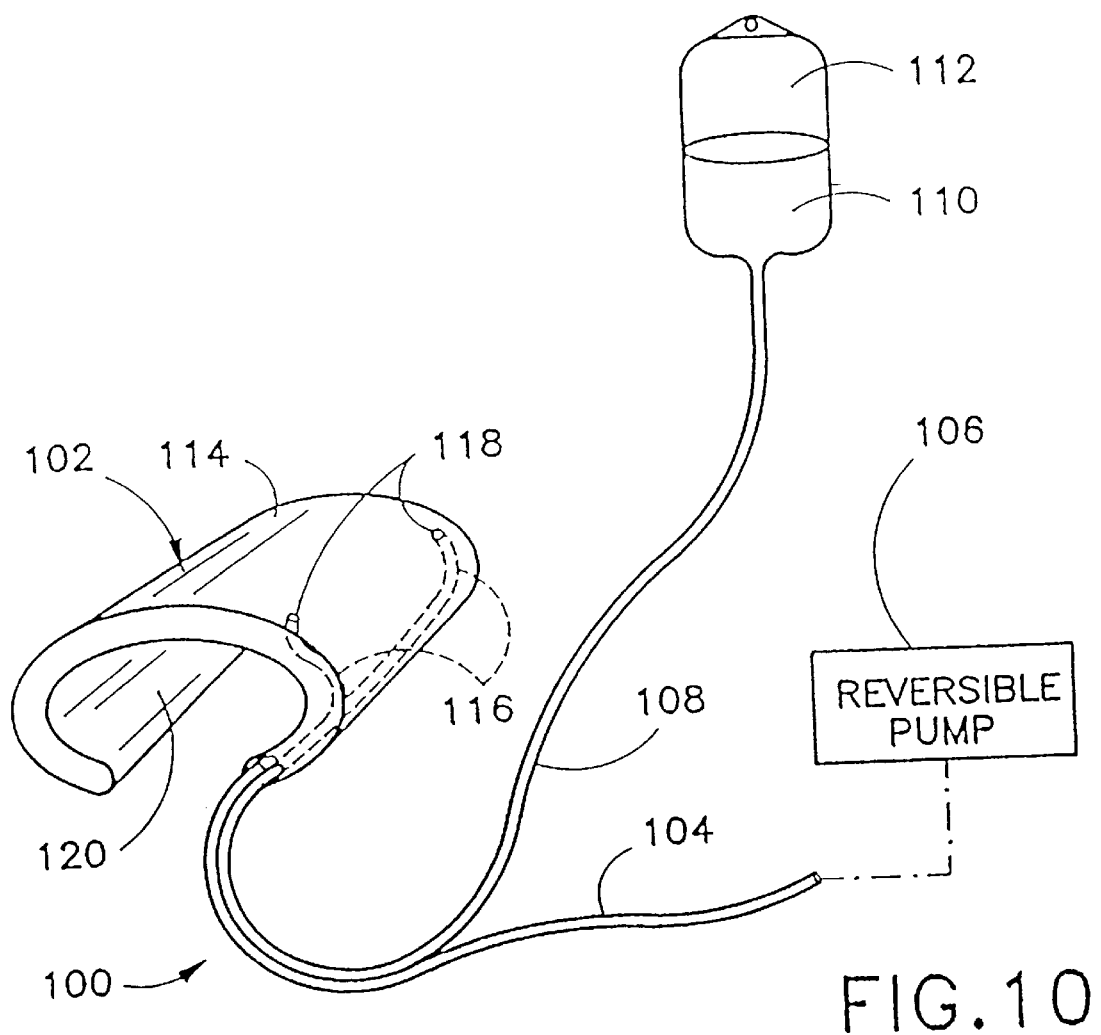
FIG. 10 is partially a schematic perspective view, on a reduced scale, and partially a block diagram of a modified intrapericardial assist or resuscitation assembly, showing an expanded intrapericardial cuff with a lubricant source operatively connected to the cuff.

As illustrated in FIG. 10, a modified intrapericardial assist device 100 comprises a balloon 102 having a predetermined size and shape in an expanded configuration so that the balloon is capable of being disposed in an intrapericardial space about a heart. Inflation componentry including a tubular member 104 and a reversible pump 106 is operatively connected to balloon 102 for inflating the balloon from an unfolded collapsed insertion configuration to the expanded configuration. Also, a feed or drip tube 108 is operatively connected to balloon 102 for delivering a lubricant 110 from a reservoir 112 to an external surface 114 of balloon 102 upon disposition of the balloon in the intrapericardial space. A manifold 116 may be provided in or along balloon 102 for delivering the lubricant 110 to a plurality of apertures or outlets 118 along surface 114. Lubricant 110 may take the form of a saline solution provided with corticosteroids for inhibiting or even preventing the formation of adhesions in the pericardial space.

The lubricating componentry of FIG. 10 may be incorporated into any of the embodiments discussed above. Conversely, componentry from the above embodiments may be added to the embodiment of FIG. 10. For example, assist device 100 may include, as shown in FIG. 2, spring elements or ribs 30 and 32 which can be bent into a curled configuration (see FIG. 3) but which tend to resume their C-shaped expanded configurations when cuff 12 is placed into an intrapericardial space during a cardiopulmonary resuscitation procedure. Spring elements or ribs 30 and 32 (FIG. 2) automatically unfurl balloon 102 (FIG. 10) from a folded collapsed configuration to an unfolded collapsed configuration.

Reversible pump 106 automatically and periodically inflates and alternately deflates balloon 102 upon a disposition thereof into the intrapericardial space. Pump 106 may include the elements illustrated in FIG. 1, namely, control unit 22, valves 16, suction source 18 and pressure source 20.

As discussed above with reference to FIG. 8, an array of electrical contacts or electrode wires 64 (FIG. 8) may be disposed on an inner contact surface 120 of balloon 102 (FIG. 10) for conducting electrical energy to the patient's heart upon an insertion of balloon 102 into the intrapericardial space. The delivery of lubricant 110 (FIG. 10) to the intrapericardial space is useful in the embodiment of FIG. 8, where a hose 70 extends to balloon 60 for maintaining the balloon in an inflated state and thereby maintaining the balloon's contact surface 62 in adequate engagement with the patient's heart during the application of electrical energy to the heart via voltage source 68, transmission leads 66 and electrical contacts or electrodes 64. Where balloon 60 must be maintained in the pericardial space for an extended period, a saline solution provided with corticosteroids is advantageously delivered to the intrapericardial space for at least inhibiting the formation of adhesions.

In assisting a malfunctioning heart with the intrapericardial assist device 100 of FIG. 10, balloon 102 is inserted into an intrapericardial space about a heart disposed in the space. Subsequently, balloon 102 is inflated in the intrapericardial space to place a compressive pressure on the heart sufficient to force blood from the heart. In addition, lubricant 110 is fed to the intrapericardial space after insertion of balloon 102 into the space. Lubricant 110 is fed to the intrapericardial space by dripping the lubricant via gravity flow along feed tube 108. The inserting of balloon 102 into the intrapericardial space is accomplished via a hypodermic type needle 34 (FIGS. 3 and 4), as discussed above with reference to FIGS. 7A–7C. The insertion may be accomplished under direct vision, where a distal end of an endoscope (not shown) is inserted into the intrapericardial space.

It is to be noted that an intrapericardial assist balloon as described hereinabove can be used not only where a heart is stopped but also where the heart is functioning poorly. For example, where a patient is a candidate for a heart transplant, a cardiac assist balloon as disclosed herein may be implanted into the intrapericardial space for an extended period of time while the patient awaits for a donor heart.

Figure 11:
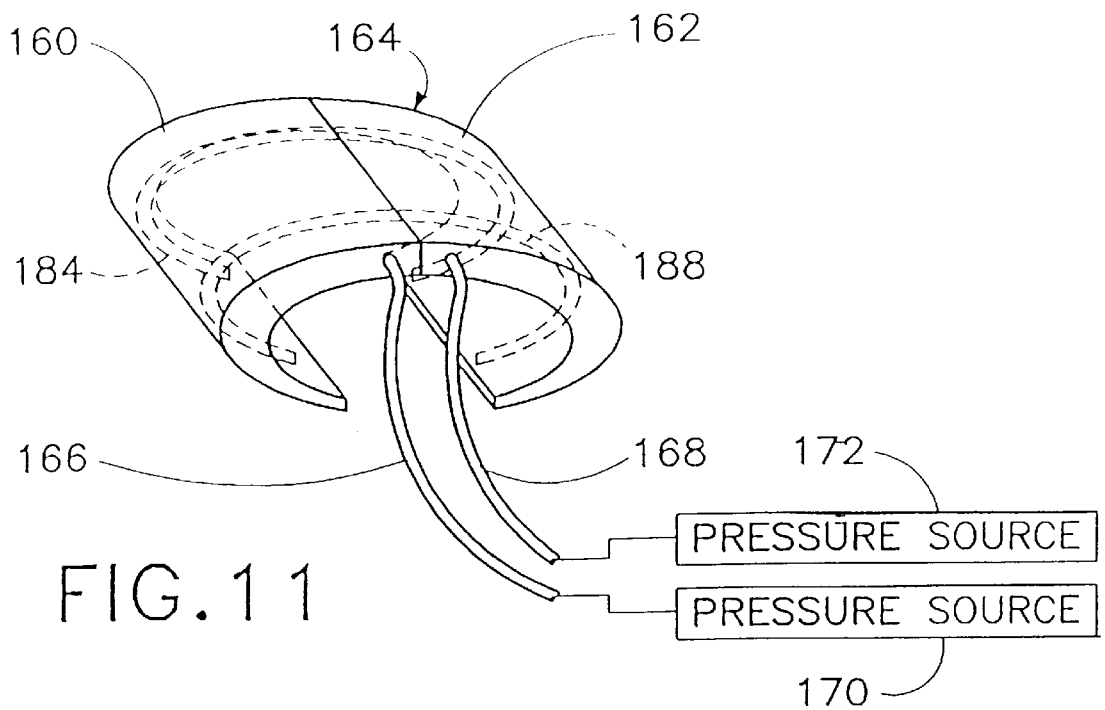
FIG. 11 is a schematic perspective view of an intrapericardial assist device.

As illustrated in FIG. 11, an intrapericardial assist device comprises a pair of alternately inflatable and collapsible balloons 160 and 162 connected to one another so that the balloons together take on a cuff configuration 164 in an inflated or expanded state, as shown in FIG. 11. Balloons 160 and 162 are connected via respective tubes 166 and 168 to respective pressure sources 170 and 172.

Figure 12:
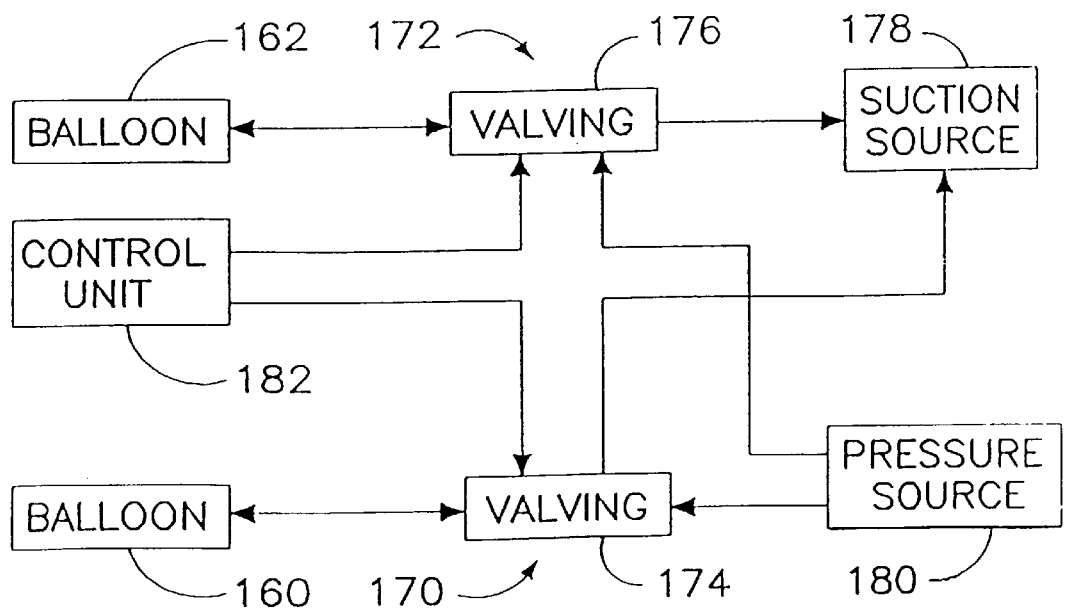
FIG. 12 is a block diagram showing functional components of the device of FIG. 11.

As illustrated in FIG. 12, pressure sources 170 and 172 each include a valve component 174 and 176. Valve components 174 and 176 are each connected to a common suction source or vacuum generator 178 and to a source 180 of pressurized fluid such as water, saline solution or a gas such as air. In response to signals from a control unit 182, valve components 174 and 176 periodically connect balloons 160 and 162 to pressure source 180 and alternately to suction source 178, whereby balloons 160 and 162 are rapidly and forcefully inflated with a predetermined periodicity.

It is to be noted that control unit 182 operates valve components 174 and 176 so as to vary the onset, the duration, and/or the rate of fluid flow to balloons 160 and 162. This measure of control enables unit 182 to differentially inflate balloons 160 and 162, for example, to different maximum pressures. Such a mode of operation is desirable when a patient is afflicted with a sticky heart valve, aortic stenosis, or other condition leading to different pressures in the two ventricles.

Control unit 182 may be provided with setting knobs (not illustrated) for varying the rates and maximum pressures that are applied to balloons 160 and 162 upon proper disposition thereof in the intrapericardial space about the heart.

Spring elements or ribs 184 and 188 are disposed in walls of balloons 160 and 162 for unfurling balloons 160 and 162 from a folded or furled configuration to an expanded configuration upon a placement of cuff 164 into an intrapericardial space.

The deployment of cuff 164 and accordingly balloons 160 and 162 is implemented according to the procedure described hereinabove with reference to FIGS. 3 and 4. The embodiment of FIGS. 11 and 12 may incorporate any of the various features described hereinabove with respect to FIGS. 1–10.

FIG. 13 illustrates a medical device 208 for use in performing surgery as discussed below with reference to FIGS. 14A through 14D to improve cardiac function in part by reducing the effective volume of the ventricles and in part by repeatedly exerting a compressive force on the reduced-volume ventricles to force blood out of the ventricles during a systolic phase of a cardiac cycle. The compressive device of FIG. 13 includes a cardiac clamp 210 in the form of a plurality of elongate prongs or tines 212 connected in a substantially circular or oval configuration to a base 214. Prongs 212 have an inherent spring bias which tends to spread the prongs into a conical configuration as depicted in FIG. 13 and 14B. Prongs 212 are each provided with at least one tooth 216 which faces inwardly relative to the spread-open conical configuration.

Device 208 further includes an inner tubular member 218 in which clamp 210 is disposed in a collapsed configuration at the onset of a surgical procedure. More specifically, clamp 210 is disposed inside a distal end portion of tubular member 218 prior to an ejection of the clamp by a distally directed motion of a rod 220. Prior to use, rod 220 may be disposed outside of tubular member 218. It is preferable, however, that rod be disposed partially inside tubular member 218 during initial deployment thereof during a cardiac operation as discussed below.

An elastic band 222 is disposed about tubular member 218 at the distal end thereof. A second tubular member 224 surrounds tubular member 218 for pushing band 222 off of the distal end of tubular member 218 as discussed below.

As illustrated in FIG. 14A, a distal end portion of tubular member 218 is inserted through parietal pericardium PP into an intrapericardial space IP surrounding a patient's heart HT. Tubular member 218 may be deployed in an open heart surgical operation or alternatively in a minimally invasive operation. In the latter case, tubular member is inserted through a thoracoscopic cannula or trocar sleeve 226.

Tubular member 218 is inserted from below the heart HT so that the distal end is pointed upwardly substantially parallel to the septum (not shown). After a proper positioning of tubular member 218, rod 220 is pushed in the distal direction, towards an apical portion AP of the heart HT to eject clamp 210, as shown in FIG. 14A. Upon the ejection of clamp 210, prongs 212 automatically spread open under their inherent spring bias to form a conical configuration. The entire instrument assembly is then moved towards heart HT so that the opened clamp 210 surrounds apical portion AP, as illustrated in FIG. 14B. Subsequently, inner tubular member 218 is pushed forward, over clamp 210, as depicted in FIG. 14C. Prongs 212 are pressed inwardly in a camming type action so that teeth 216 bite into the myocardium of heart HT and anchor clamp 210 thereto. Continued forward or distal motion of inner tubular member 218 relative to clamp 210 serves to compress apical portion AP of heart HT, as shown in FIG. 14C. To some extent, prongs 212 pivot about the connecting points to base 214 in response to the camming action of tubular member 218.

After the positioning and partial closure of clamp 210 about the apical portion AP of heart HT, outer tubular member 224 is shifted in the distal direction toward heart, while clamp 210 and inner tubular member 218 are maintained in position about apical heart portion AP. This relative motion serves to slide or push elastic band 222 off of tubular member 218 and onto the closed clamp 210. As illustrated in FIG. 14D, band 222 is left in place on clamp 210 to hold pongs 212 in a partially closed configuration compressing apical portion AP of heart HT and reducing the volume of both ventricles of the heart. The reduced volume makes the pumping action of the heart more efficient and improves blood circulation in individuals suffering from congestive heart failure or left ventricular hypertrophy.

As further illustrated in FIG. 14D, a cuff-shaped balloon 228 is positioned in the intrapericardial space IP generally above the closed clamp 210. A tube 230 extends from balloon 228 to a pressure source (not illustrated). The structure, function and deployment of balloon 228 are as discussed above, for instance, with reference to FIGS. 1–10. In most cases, balloon 228 is repeatedly and forcibly inflated to squeeze blood from the ventricles (not shown) of heart HT to assist in pulsatile blood circulation.

Figure 15:
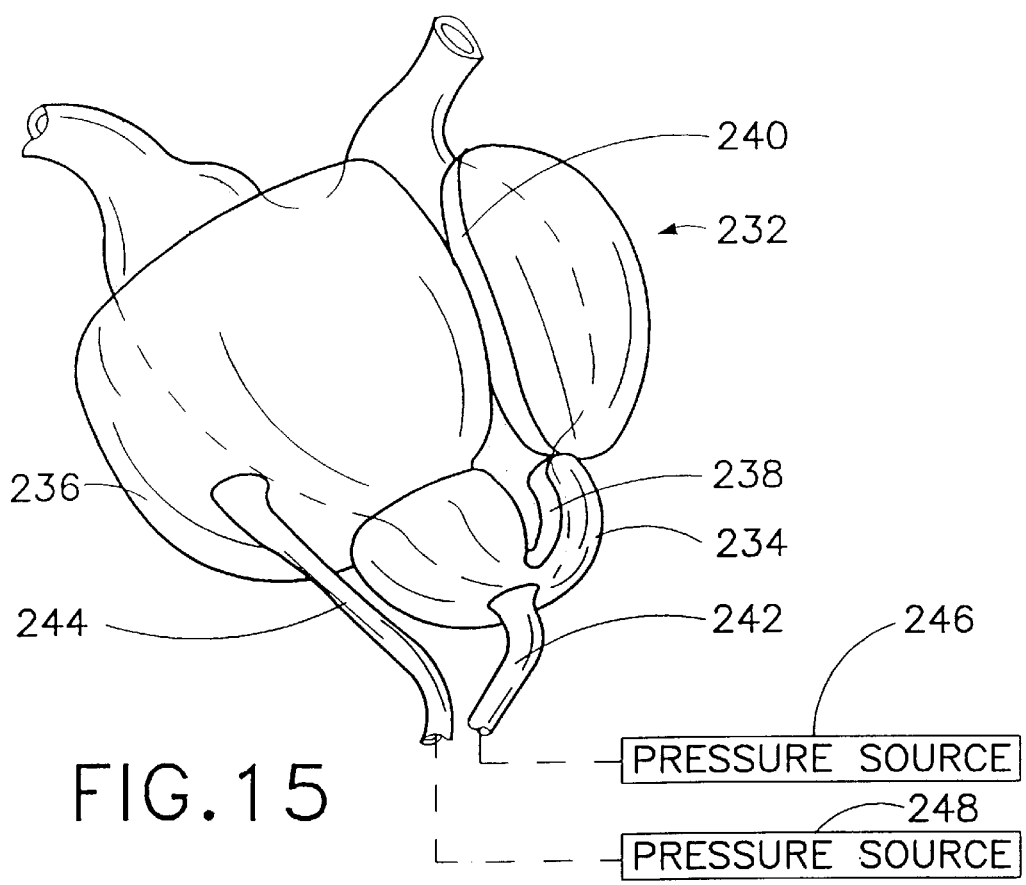
FIG. 15 is a schematic view of a dual balloon device disposed in a patient's intrapericardial space about the patient's heart for assisting cardiac function.

As illustrated in FIG. 15, a cardiac assist device 232 comprises a first balloon 234 and a second balloon 236. Balloons 234 and 236 are optionally connected to one another and positioned in an intrapericardial space (not shown) in a single deployment or insertion operation. Balloon 234 assumes a generally cup shape in an inflated configuration, while balloon 236 assumes a generally cylindrical configuration when inflated. Balloons 234 and 236 are formed with slots or gaps 238 and 240 for purposes of facilitating disposition about heart HT. Tubes 242 and 244 extend from balloons 234 and 236 to respective pressure sources 246 and 248. Pressure source 248 periodically or repeatedly inflates and alternately deflates balloon 236 during a cardiac assist operation, while pressure source 246 functions to inflate balloon 234 and to maintain that balloon in its expanded configuration during the cyclic inflation and deflation of balloon 236.

Figures 16A, 16B:
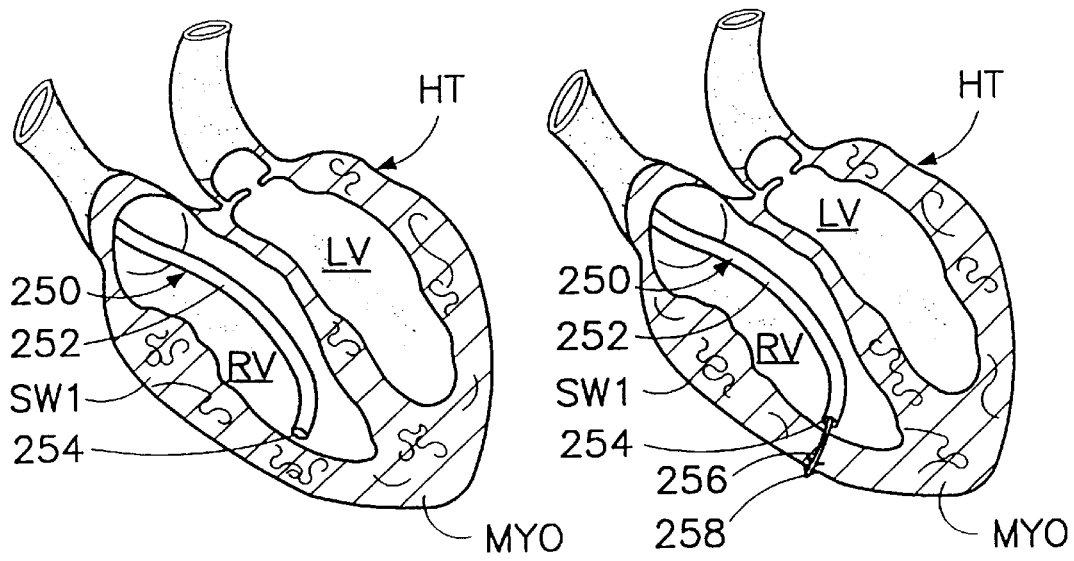
FIGS. 16A–16F are a series of schematic cross-sectional views of a patient's heart, showing successive steps in an alternative technique for reducing ventricular volume as part of a complete procedure for improving cardiac function.
Figure 16C:
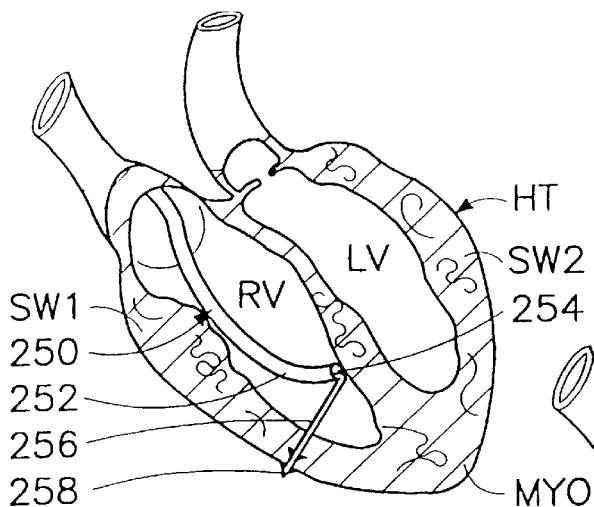
Figure 16D:
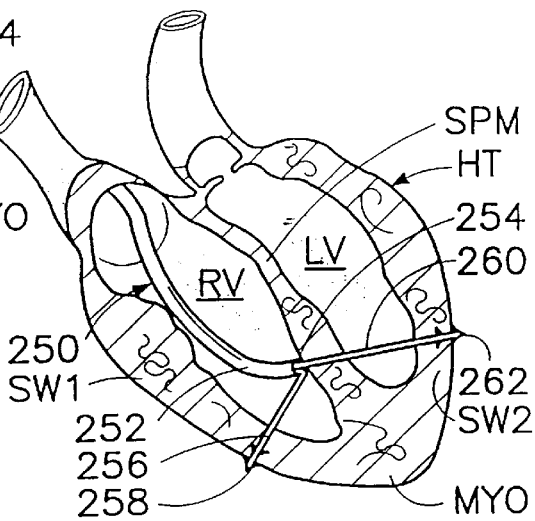
Figure 16E:
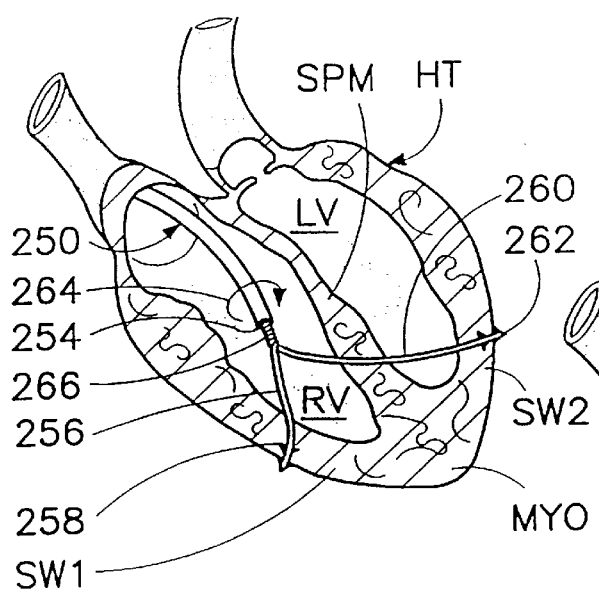
Figure 16F:
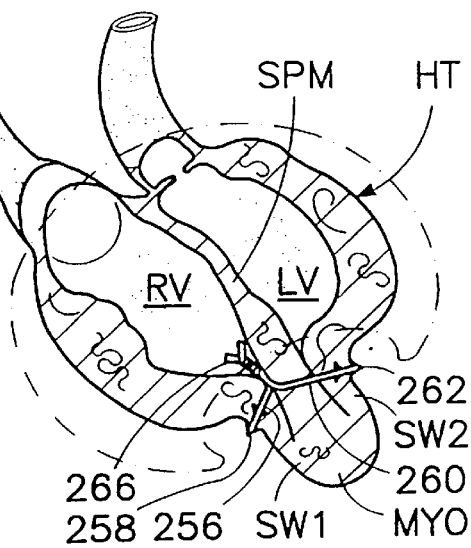

FIG. 16A through 16F illustrate an alternative procedure for reducing ventricular volume in a cardiac assist operation. As shown in FIG. 16A, a catheter 250 is inserted through a patient's vascular system into one of the ventricles LV and RV of the patient's heart HT, for example, the right ventricle RV. Catheter 250 has a leading end portion 252 which is steerable to enable a directing of a mouth opening 254 toward a sidewall SW1 of the patient's myocardium MYO. As shown in FIG. 16B, a wire 256 is ejected from catheter 250 through mouth opening 254 into and partially through myocardial sidewall SW1 upon a positioning of the mouth opening adjacent to the sidewall. Wire 256 is provided at a leading end with a plurality of barbs or arrow heads 258 preventing a withdrawal of the wire along its insertion path through myocardial sidewall SW1. Upon an embedding of barbs 258 in myocardial sidewall SW1, catheter 250 is manipulated to steer leading end portion 252 towards cardiac septum SPM, as illustrated in FIG. 16C. Then a second wire 260 is ejected from catheter 250 through mouth opening 254 and septum SPM into and partially through an opposing myocardial sidewall SW2, as depicted in FIG. 16D. Wire 260 is provided at a leading end with a plurality of barbs or arrow heads 262 preventing a detachment of the wire from myocardial sidewall SW2. Upon an embedding of barbs 262 in myocardial sidewall SW2, catheter 250 and wires 256 and 260 are manipulated to twist wires 256 and 260 about one another, as indicated by an arrow 264 and wire coils 266 in FIG. 16E. This twisting action exerts tension on wires 256 and 260 and is performed until sidewalls SW1 and SW2 are drawn sufficiently close to one another, as shown in FIG. 16F, to effectively reduce the volumes of ventricles RV and LV. Wires 256 and 260 are thereafter severed by any practicable technique including but not limited to shearing, laser cutting, etc. A cuff-shaped balloon 268 may then be deployed and operated as discussed above with reference to FIGS. 1–10, 14D and 15.

A cardiac assist device as described above may additionally be provided with an ultrasonic sensor for use in monitoring blood flow in and/or from the ventricles upon deployment of the cardiac assist device. The ultrasonic (Doppler) sensor may be attached to the cardiac assist device, for instance, to the pulsating balloon.

Figure 17A:
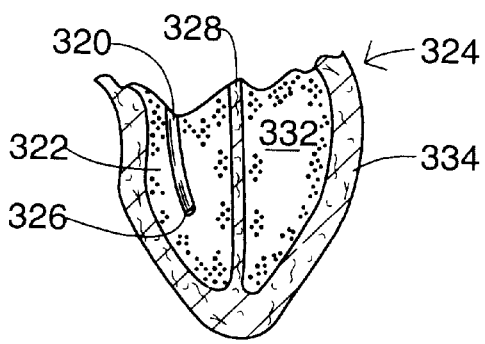
FIGS. 17A through 17D are partial schematic cross-sectional views of a human heart, showing successive steps in a method for reducing ventricular volume.

As illustrated in FIG. 17A, a method for reducing ventricular volume to improve cardiac functioning includes a step of inserting a distal or leading end portion of a catheter 320 through the vascular system of a patient, and particularly through the vena cava, into the right ventricle 322 of the patient's heart 324. The deployment of catheter 320 is carried out according to procedures that are well known in the art. For example, the catheter 320 may be introduced over a guide wire (not shown) which has been previously threaded through the venous system to the right ventricle 322.

Figure 17B:
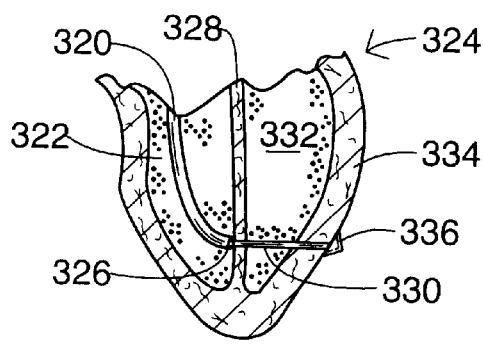

After the distal end portion of catheter 320 has been inserted through the right auricle (not shown) into the right ventricle 322, the catheter is manipulated to place a leading end or tip 326 of catheter 320 into engagement with a lower part of a septum 328 of the patient's heart 324, as shown in FIG. 17B. A compressive cardiac implant or insert in the form of a tensile member 330 such as a wire or a stiff suture is then forcibly ejected from the catheter 320 through septum 328, a lower part of the patient's left ventricle 332, and a generally left wall or myocardium region 334 of the patient's heart 324.

As further illustrated in FIG. 17B, tensile member 330 is formed at a leading end with an anchor 336 in the form of a barb or flange. Anchor 336 has a structure which permits movement of the anchor in one direction through cardiac tissues and prohibits movement of the anchor in the opposite direction through the tissue. For instance, anchor 336 may be hinged to the leading end of tensile member 330 and formed with a stop for arresting rotational motion beyond a predetermined orientation relative to tensile member 320. Prior to the ejection of tensile member 330 from catheter 320, anchor 336 is disposed in a collapsed configuration inside catheter 320. Anchor 336 essentially maintains this collapsed configuration during the ejection process.

Figure 17C:
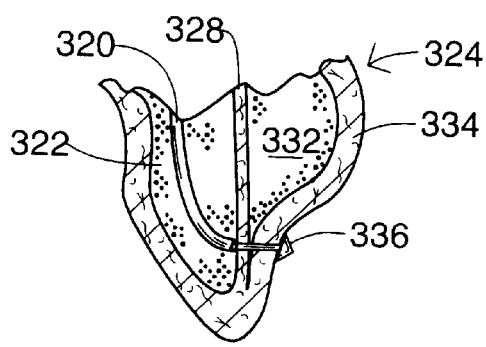

After anchor 336 has passed through heart wall 334, a retraction force is applied to tensile member 330 tending to draw the tensile member back in the catheter 320. As shown in FIG. 17C, this action results in the planting of anchor 336 along the outer side of wall 334 and a drawing together of the lower parts of septum 328 and wall region 334. Septum 328 and heart wall 334 are thus brought into at least approximate contact with one another to effectively close off a lower or apical portion of heart 324, as illustrated in FIG. 17C.

Figure 17D:
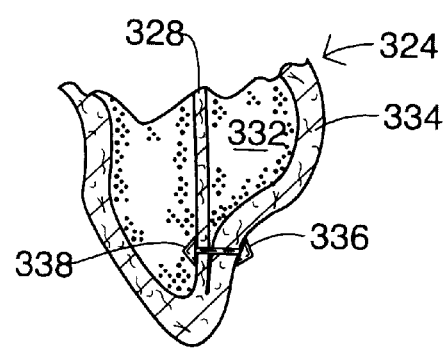

After the limited retraction of tensile member 330 and the consequent closure of the lower or apical portion of heart 324, tensile member 330 is provided with a second anchor 338, as shown in FIG. 17D, and severed on a side of septum 328 inside right ventricle 322. Anchor 338 may be similar in structure to anchor 336 (but oppositely biased) and permanently attached thereto. In that case, tensile member 330 with anchors 336 and 338 is preselected, prior to insertion in catheter 320, to match the particular heart 324 and deployment location. More specifically, tensile member 330 and anchors 336 and 338 together define a preformed compressive cardiac implant having an interanchor spacing equal to the combined thickness of septum 328 and heart wall 334 at the intended point of deployment of the cardiac implant. The thicknesses of septum 328 and heart wall 334 may be premeasured by a CAT scan or magnetic resonance imaging or through radiographic investigation. Anchor 338 is held in a collapsed configuration by a sleeve (not shown) inside catheter 320, thus enabling a relative motion of anchor 338 in a distal direction (relative to the operator or surgeon) during an implantation operation.

In an alternative structure and method of deployment, anchor 338 is permanently fixed to tensile member 330 only after the ejection of tensile member 330 through septum 328, left ventricle 332, and heart wall 334. Prior to the ejection operation, anchor 338 is housed inside catheter 330 and surrounds tensile member 330. After ejection of tensile member 330, anchor 338 is pushed by an ancillary tubular member (not shown) into contact with the right-ventricle side of septum 328. Anchor 338 is then secured to tensile member 330 by any suitable means. For instance, where tensile member 330 and anchor 338 are made of thermosetting resin or polymeric material, a piezoelectric crystal may be inserted into right ventricle 322 through catheter 320 to ultrasonically weld anchor 338 to tensile member 330. Alternatively, tensile member 330 may be formed with a series of spaced beads and anchor 38 made of an elastic biocompatible material, so that anchor 338 may be pushed over one or more of the beads and locked to tensile member in a snap-lock fit.

The severing of tensile member 330 on a side of anchor 338 opposite septum 328 is effectuated by any suitable means. A cutting device (not shown) may be inserted into right ventricle 322 and subsequently removed therefrom via catheter 320. Possible kinds of cutting devices for this application have jaws (not shown) or an ultrasonically actuated blade (not shown). Alternatively, catheter 320 might be rotated about its longitudinal axis to effectuate a twisting separation of tensile member 330.

Figure 18A:
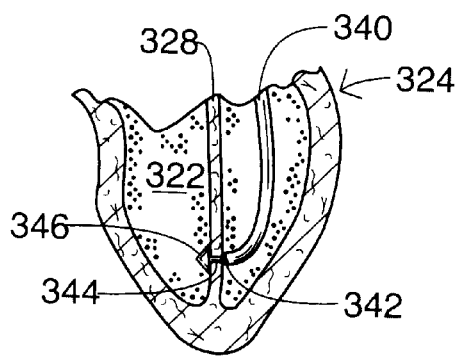
FIGS. 18A through 18F are partial schematic cross-sectional views of a human heart, showing successive steps in another method for reducing ventricular volume.

As illustrated in FIG. 18A, another method for reducing ventricular volume to improve cardiac functioning of the patient's heart 324 includes a step of inserting a distal or leading end portion of a catheter 340 through the vascular system of the patient, and particularly through the aorta (not shown), into the left ventricle 332 of the heart 324. Again, the particulars of deploying deployment catheter 340 are well known in the art.

Figure 18B:
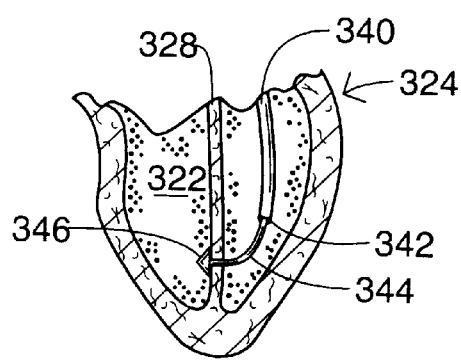

After the distal end portion of catheter 340 has been inserted through the left auricle (not shown) into the left ventricle 332, the catheter is manipulated to place a leading end or tip 342 of catheter 340 into engagement with a lower part of a septum 328 of the patient's heart 324, as shown in FIG. 18A. A compressive cardiac implant or insert segment in the form of a tensile member or wire 344 is then forcibly ejected from the catheter 340 through septum 328, as depicted in FIG. 18B. Tensile member 344 is formed at a leading end with an anchor 346 in the form of a barb or flange. As discussed above with reference to anchor 336, anchor 346 has a structure which permits movement of the anchor in one direction through cardiac tissue and prohibits movement of the anchor in the opposite direction through the tissue. Again, anchor 346 may be hinged to the leading end of tensile member 344 and formed with a stop for arresting rotational motion beyond a predetermined orientation relative to tensile member 344. Prior to the ejection of tensile member 344 from catheter 340, anchor 346 is disposed in a collapsed configuration inside catheter 40. Anchor 346 essentially maintains this collapsed configuration during the ejection process.

Figure 18C:
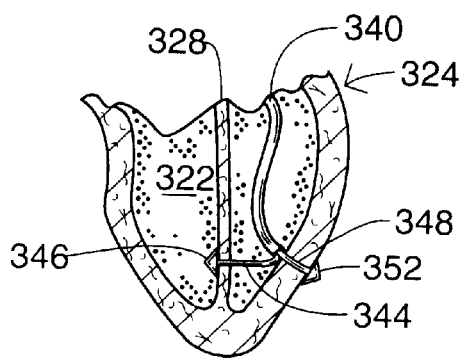

After the piercing of septum 328 by tensile member 344, catheter 340 is withdrawn slightly, as shown in FIG. 18B. Then, catheter 340 is manipulated to place end or tip 342 into engagement with a lower part of heart wall 334, as shown in FIG. 18C. A second compressive cardiac implant or insert segment in the form of a tensile member or wire 348 is then forcibly ejected from the catheter 40 through heart wall 334, as depicted in FIG. 18C. Tensile member 348 is also formed at a leading end with an anchor 350 in the form of a barb or flange.

Figure 18D:
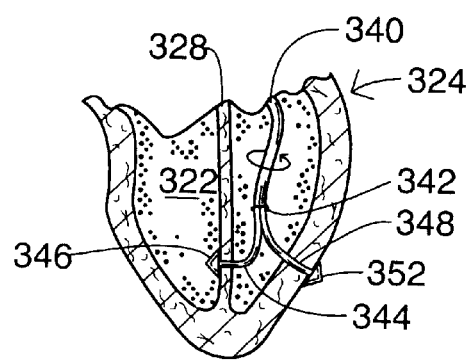
Figure 18E:
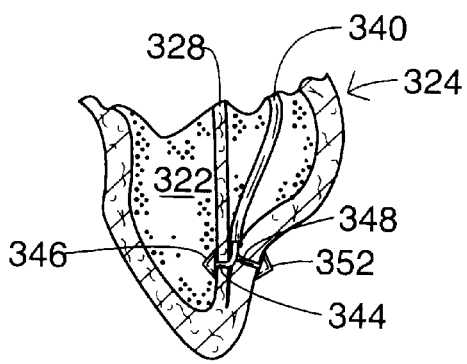
Figure 18F:
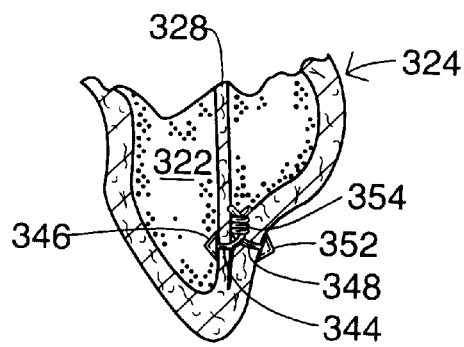

After the piercing of heart wall 334 by tensile member 348, catheter 340 is again pulled back slightly to a position depicted in FIG. 18D. At that juncture, catheter 340 is turned about its longitudinal axis, as indicated by an arrow 352, to twist tensile members or wire segments 344 and 348. Catheter 340 may be provided at its leading end with a cross-bar (not shown) to facilitate the twisting of tensile members or wire segments 344 and 348 about one another, tensile members or wire segments 344 and 348 extending on opposite sides of the cross-bar. The twisting of tensile members or wire segments 344 and 348 draws septum 328 and heart wall 334 together, as shown in FIG. 18E. Eventually, the twisting results in severing of tensile members or wire segments 344 and 48 so that they are joined to one another by a twist knot 354.

Figure 19:
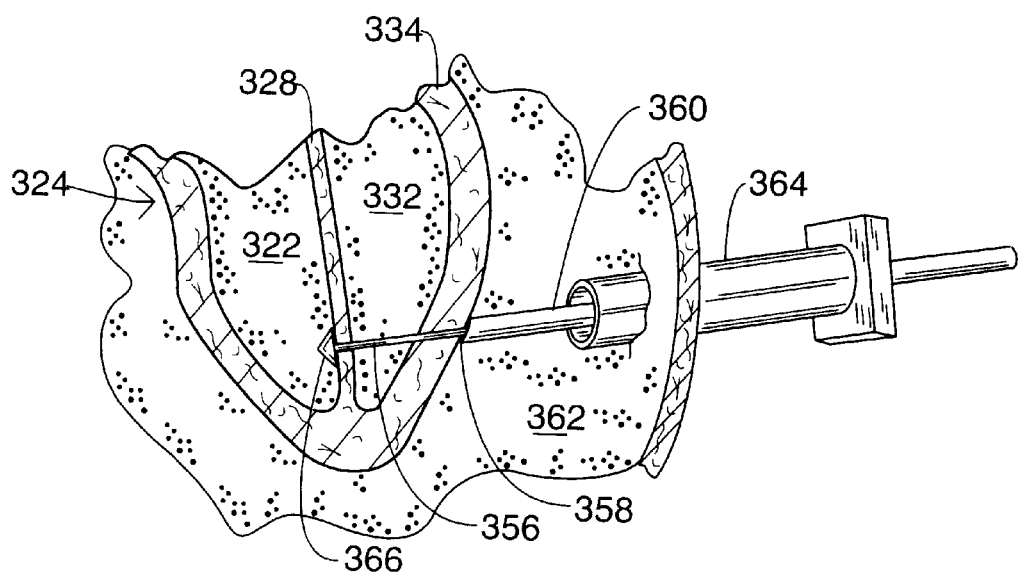
FIG. 19 is a partial schematic cross-sectional views of a human heart, showing a step in yet another method for reducing ventricular volume.

As shown in FIG. 19, a compressive cardiac implant of insert 356 in the form of a tack is ejected from a free end 358 of a tubular applicator 60 through heart wall 334, left ventricle 332, and septum 328. Applicator 360 is inserted into an intrapericardial space 362 through a thoracoscopic cannula or trocar sleeve 364. Tack 356 is formed at a leading end with an anchor 366 in the form of a barb or flange. Anchor 366 has a structure which permits movement of the anchor in one direction through cardiac tissues and prohibits movement of the anchor in the opposite direction through the tissue.

After the ejection of tack 356 through ventricle 332, a tensile force is placed on tack 356 to draw the tack in a reverse direction and thereby compress the lower portion or apex of ventricle 332 between anchor 366 and the leading end of tubular applicator 360. After the limited retraction of tack 356 and the consequent closure of the lower or apical portion of heart 324, tack 356 is provided with a second anchor (not shown) and severed on a side of heart wall 334 inside the intrapericardial space 362. Where this second, closure, anchor is in the form of a resilient collar and where tack 356 is provided with a series of beads (not shown), the collar may be forced over the beads in seriatim to provide a proper clamping force on the cardiac tissues at the lower end or apex of ventricle 332, thereby bringing septum 328 and heart wall 334 into close proximity (if not actual contact) with one another and thus substantially closing the apical portion of ventricle 332.

Figure 20:
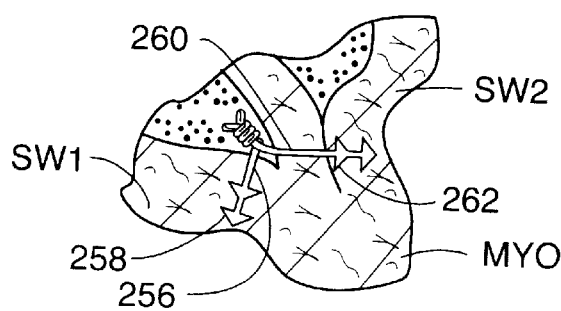
FIG. 20 is a partial cross-sectional view of an apical portion of a human heart, showing an alternative procedure for reducing ventricular volume.

FIG. 20 illustrates a modification of the procedure described hereinabove with reference to FIGS. 16A through 16F. Wires 256 and 260 are ejected from mouth opening 254 of catheter 250 so that free ends of wires 256 and 260, including barbs 258 and 262, are completely embedded in outer sidewalls SW1 and SW2 of the myocardium MYO. The free ends of wires 256 and 260, including barbs 258 and 262, are completely surrounded by the myocardium MYO so that the implanted compressive or tensile device is contained entirely within the heart and does not protrude into the intrapericardial space (not shown).

Figure 21:
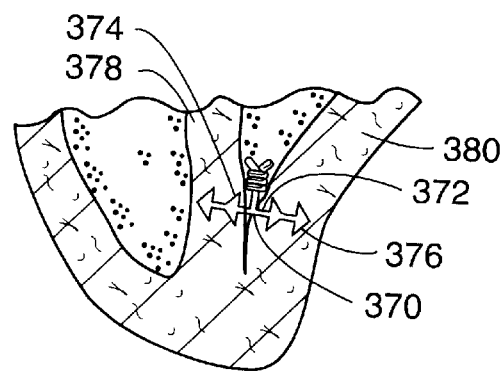
FIG. 21 is a partial cross-sectional view of an apical portion of a human heart, showing another alternative procedure for reducing ventricular volume.

FIG. 21 illustrates an analogous modification of the procedure discussed above with reference to FIGS. 18A through 18F. Free ends of wires or tensile members 370 and 372, provided with plural barbs or teeth 374 and 376, are completely embedded in a septum 378 and an outer wall 380 of a patient's heart. The free ends of wires 370 and 372, including barbs 374 and 376, are completely surrounded by the septum 378 and the outer heart wall 380 so that the implanted compressive or tensile device is contained entirely within the heart and does not protrude into the intrapericardial space (not shown).

A like modification (not specifically illustrated) may be made in the technique depicted in FIGS. 17A though 17D. In that case, only the barbed end 336 of wire 330 is embedded completely within heart tissue. The trailing anchor 338 remains in communication with the right ventricle 322 of the patient. In any event, the implanted compressive or tensile device is contained entirely within the patient's heart and does not protrude into the intrapericardial space.

Although the invention has been described in terms of particular embodiments and applications, one of ordinary skill in the art, in light of this teaching, can generate additional embodiments and modifications without departing from the spirit of or exceeding the scope of the claimed invention. For example, there are alternative methods for inserting a balloon type cardiac assist device into the intrapericardial space. Such alternative methods include placing the balloon(s) through a laparoscopic cannula inserted either through the rib cage and alongside the sternum, or below the rib cage and above the diaphragm. The installation of an intrapericardial assist device may be accomplished nearly under direct vision, through a small incision beneath the ribs, without splitting any ribs.

Furthermore, other mechanisms for closing a compressive device about a lower end of a patient's heart will be apparent to those skilled in the art. Such mechanisms will generally contemplate the conversion of an axially directed force to a compressive force. In one alternative design, instead of pushing tubular member 218 about the expanded clamp 210, a screw mechanism may be used to close, and possibly open, prongs 212. In another alternative design, a cup-shaped clamp has a plurality of relative movable leaves, as in a mechanical iris.

It is to be noted, in addition, that device 208 may be used to place clamp 210 about a part of the heart HT other than apical portion AP. Thus, device 208 may approach the heart HT from a different direction, for example, where it is desired to reduce the effective volume of the left ventricle only.

Prongs 212 may be spring biased to close clamp 210. In that case, the inserting instrument is adapted to spread prongs 212 into a opened configuration in opposition to the action of inherent spring forces. When the opening force is removed, the clamp squeezes the hear muscle and compresses a portion of the heart.

A catch may be provided on prongs 212 for holding band 222 on clamp 210 after the disposition of band about the clamp.

Accordingly, it is to be understood that the drawings and descriptions herein are proffered by way of example to facilitate comprehension of the invention and should not be construed to limit the scope thereof.

What is claimed is:

1. A surgical method for assisting cardiac function, comprising:
    inserting a device into a patient; and
    applying said device to a lower end portion of the patient's heart so as to compress and at least partially close a lower portion of at least one ventricle of the heart, said device including a wire provided at a free end with at least one anchoring barb, the applying of said device to the lower portion of the patient's heart including:

inserting a catheter into a ventricle of the patient's heart;

ejecting said free end of said wire from said catheter into the patient's myocardium so that said free end and said at least one barb are embedded in the myocardium, surrounded thereby; and exerting tension on said wire to pull walls of the patient's heart towards one another so as to compress and close off said lower portion of said at least one ventricle of the heart.

2. The method defined in claim 1 wherein said free end of said wires is one of a pair of free wire ends each provided with at least one barb, the applying of said device to the lower portion of the patient's heart including:

ejecting said free wire ends from said catheter into the patient's myocardium so that said free ends and the respective barbs thereof are embedded in the myocardium, surrounded thereby, and exerting tension on said wire ends to pull said walls of the patient's heart towards one another so as to compress and close off said lower portion of said at least one ventricle of the heart.

3. The method defined in claim 2 wherein said wire ends are terminal portions of wire segments, the exerting of tension on said wire ends includes twisting said wire segments about one another.

4. The method defined in claim 2 wherein said walls are outer walls of the patient's heart, the applying of said device serving to compress and at least partially close lower portions of two ventricles.

5. The method defined in claim 2 wherein one of said walls is an outer wall of the patient's heart while another of said walls is a septum of the patient's heart, the applying of said device serving to compress and at least partially close a lower portion of exactly one ventricle.

6. The method defined in claim 1 wherein the ejecting said free end of said wire from said catheter into the patient's myocardium includes forcing said free end of said wire through a septum of the patient and into an outer wall of the patient's heart, said walls being said septum and said outer wall, the applying of said device serving to compress and at least partially close a lower portion of exactly one ventricle.

7. The method defined in claim 1, further comprising:

additionally inserting at least one balloon into an intrapericardial space about the patient's heart; and inflating said balloon in said intrapericardial space to place a compressive pressure on the patient's heart sufficient to force blood from the heart.

8. The method defined in claim 7 wherein said device is applied to said lower portion of the patient's heart prior to the inflating of said balloon.

9. The method defined in claim 8, further comprising periodically inflating and alternately deflating said balloon to pump blood from said heart in pulsatile fashion.

10. The method defined in claim 9, further comprising maintaining said device applied to the patient's heart to maintain said lower portion of said at least one ventricle of the patient's heart compressed and closed off during the periodic inflating and deflating of said balloon.

11. The method defined in claim 7 wherein the inserting of said balloon includes providing a hypodermic type needle, inserting said needle through a skin surface and into said intrapericardial space, and injecting said balloon in a collapsed configuration into said intrapericardial space.

12. The method defined in claim 7, further comprising periodically inflating said balloon upon inserting of said balloon into said intrapericardial space.

13. The method defined in claim 7 wherein said balloon has an arcuate cuff configuration in an inflated configuration, the inflating of said balloon including shaping said balloon into said arcuate configuration.

14. The method defined in claim 7 wherein the inserting of said device includes inserting said device through a trocar sleeve or cannula.

15. A method for reducing ventricular volume, comprising:

inserting a catheter into a ventricle of a patient's heart;

deploying a tensile member from a leading end of said catheter;

attaching said tensile member to the patient's heart so that said tensile member is contained completely within the patient's heart and does not protrude therefrom; and exerting tension on said tensile member to draw walls of the patient's heart towards one another to reduce the volume of at least one ventricle of the patient's heart.

16. The method defined in claim 15 wherein said tensile member is provided with at least one barb at a leading end, the attaching of said tensile member to the patient's heart including embedding said barb in the patient's heart.

17. The method defined in claim 15 wherein said tensile member is one of two tensile members, further comprising attaching the other tensile member to the patient's heart, the exerting of tension on said one of said tensile members including twisting the tensile members about one another.

18. The method defined in claim 15 wherein said walls are outer walls of the patient's heart, the attaching of said tensile member to the patient's heart and the exerting tension on said tensile member serving to compress and at least partially close lower portions of two ventricles.

19. The method defined in claim 15 wherein one of said walls is an outer wall of the patient's heart while another of said walls is a septum of the patient's heart, the attaching of said tensile member to the patient's heart and the exerting tension on said tensile member serving to compress and at least partially close a lower portion of exactly one ventricle.

* * * * *

Adverse Decisions in Interference

Patent No. 6,572,529, Wilk J. Peter, INTRAPERICARDIAL ASSIST METHOD, Interference No. 105,598, final judgment adverse to the patentees rendered June 12, 2008, as to claims 15-19.

*(Official Gazette February 3, 2009)*